United States Patent
Hamann et al.

(12)

(10) Patent No.: US 6,900,195 B2
(45) Date of Patent: May 31, 2005

(54) MANZAMINES FOR TREATMENT OF DRUG RESISTANT INFECTION

(75) Inventors: Mark T. Hamann, University, MS (US); Khalid El-Sayed, University, MS (US)

(73) Assignee: The University of Mississippi, University, MS (US)

( * ) Notice: Subject to any disclaimer, the term of this patent is extended or adjusted under 35 U.S.C. 154(b) by 0 days.

(21) Appl. No.: 10/362,400

(22) PCT Filed: Aug. 29, 2001

(86) PCT No.: PCT/US01/27035
§ 371 (c)(1),
(2), (4) Date: Jul. 22, 2003

(87) PCT Pub. No.: WO02/17917
PCT Pub. Date: Mar. 7, 2002

(65) Prior Publication Data
US 2004/0019029 A1 Jan. 29, 2004

Related U.S. Application Data

(60) Provisional application No. 60/228,892, filed on Aug. 29, 2000.

(51) Int. Cl.$^7$ ................................................ A01N 43/00
(52) U.S. Cl. ...................................................... 514/183
(58) Field of Search ................................. 514/183, 281

(56) References Cited

U.S. PATENT DOCUMENTS 6,143,756 A * 11/2000 Kara et al. .................. 514/281

* cited by examiner

Primary Examiner—Alton Pryor
(74) Attorney, Agent, or Firm—Greenberg Traurig LLP; Eugene C. Rzucidlo

(57) ABSTRACT

A method of treating an infectious disease or condition in a subject in need of such treatment is disclosed. The method comprises administering to a subject an effective amount of a manzamine, manzamine derivative or analog or an optical isomer or racemate or tautomer thereof or a pharmaceutically acceptable salt thereof.

3 Claims, 2 Drawing Sheets

MANZAMINES FOR TREATMENT OF DRUG RESISTANT INFECTION

CROSS-REFERENCE TO RELATED APPLICATION

This application claims priority from U.S. Provisional Application 60/228,892, filed Aug. 29, 2000.

UNITED STATES GOVERNMENT FINANCIAL SUPPORT

This work is supported at least in part by grants from the National Institute of Health of the United States of America 2R01AI36596, 5R29AI36596 and 5K02AI01502. The Government of the United States may have certain rights in this invention.

WORLD HEALTH ORGANIZATION FINANCIAL SUPPORT

This work is supported at least in part by a grant from the World Health Organization of the United Nations 90194.

FIELD OF THE INVENTION

The present invention relates to the use of sponge-derived alkoloids known as "manzamines" as well as derivatives and analogs thereof in the treatment of infectious diseases. It has been found that manzamines as well as derivatives and analogs thereof are useful as antiparasitics, antimicrobials/bacteriology, antivirals and against opportunistic infections (mycology). Three new manzamine derivatives are also disclosed.

BACKGROUND OF THE INVENTION

The AIDS opportunistic infection tuberculosis infects one-third of the world's population and, with malaria, ranks among the 12 leading causes for loss of Disability-Adjusted Life Years ("DALYs"). The rapid spread of drug-resistant strains of tuberculosis and malaria, coupled with the extremely limited numbers of drugs available to treat these diseases, has created an urgent need for novel therapeutic agents with new modes of action to counter these impeding threats.

Despite a significant mortality reduction in the United States and Europe from infectious diseases over the last century the last two decades have shown mortality increases that indicate the need for constant vigilance. See, Armstrong, G. L.; Conn, L. A.; Pinner, R. W., "Trends in Infectious Disease Mortality in the United States During the 20th Century," JAMA 1999, 281, 61–66. An unforeseeable trend from 1980 to the early 1990's resulted in an astonishing 58% increase in mortality rates associated with infectious diseases. Numerous spikes in the mortality rates over the last century from infectious diseases indicate how quickly a contagious disease can move through a population. The seriousness is further compounded with increases in drug resistance and outbreaks of diseases like avian influenza that have no previous history of being infective to humans. See, "Centers for Disease Control and Prevention, Update: Isolation of Avian Influenza A (H5N1) Viruses From Humans in Hong Kong," 1997–98, *Morbidity and Mortality Weekly Reports* 1998, 46, 1245–47.

The risk of malaria now exists in 100 countries and territories, with 92 of these facing the malignant form of the disease (*Plasmodium falciparum*). Over 45% of the world population lives in areas of the world where malaria is endemic. Globally, there are 300–500 million clinical cases annually, with 1.5–2.7 million deaths associated with malaria. See, http://www.who.int/ctd/html/malaria.html (2000). Most of the annual deaths occur among children under five years of age. Despite the initial success of the World Health Organization's program to eradicate malaria globally during the 1950's and 1960's, it has become increasingly clear that these attempts have faltered due to increasing resistance of the malarial parasites to commonly used drugs and of the mosquito to insecticides. The estimated number of new infections has now reached their original levels, many of these being "malignant" malaria caused by the most dangerous malarial parasite, *P. falciparum*.

In recent years the marine environment has emerged as a promising source for new lead drugs to combat this devastating disease. See, El Sayed, K. A.; Dunbar, C. D.; Goins, K. D.; Cordova, C. R.; Perry, T. L.; Wesson, K. J.; Sanders, S. C.; Janus, S. A.; Hamann, M. T. The Marine Environment: A Resource for Prototype Antimalarial Agents, *J. Nat. Toxins.* 1996, 5, 261–285; Nasu, S. S.; Yeung, B. K. S.; M. T. Hamann; Scheuer, P. J.; Kelly-Borges, M.; Goins, K. D, Puupehenone-Related Metabolites From Hawaiian Sponge, Hyrtios spp., *J. Org. Chem.* 1995, 60, 7290–7292. The fairly common and easily isolated marine alkaloids known as the manzamines show dramatic and unexpected improvements in activity against malaria in mice as noted above. See, Ang, K. K. H.; Homes, M. J.; Higa, T.; Hamann, M. T.; Kara, U. A. K., "In vivo Antimalarial Activity of the Beta-Carboline Alkaloid Manzamine A," *Antimicrob. Agents and Chemother.* 2000, 44, 1645–1649.

Although malaria is not considered an opportunistic infection in HIV-infected patients it has been shown that HIV positive individuals are more susceptible to *P. falciparum* and become more symptomatic. See, Verhoeff, F. H.; Brabin, B. J.; Hart, C. A.; Chimsuku, L.; Kazembe, P.; Broadhead, R. L., "Increased Prevalence of Malaria in HIV-Infected Pregnant Women and its For Malaria Control," *Trop Med Int Health* 1999, 4, 512. See also, French, N.; Gilks, C., "HIV and malaria, do they interact?," *Trans R Soc Trop Med Hyg* 2000, 94, 23337. In addition, plasma viral loads have been shown to be higher in acutely infected malaria patients with HIV (see, Hoffman, I. F.; Jere; C. S.; Taylor, T. E., "The Effect of *Plasmodium falciparum* Malaria on HIV-1 RNA Blood Plasma Concentration, AIDS 1999, 13, 487494) and malaria infections have been shown to induce virus expression in HIV transgenic mice. See, Freitag, C.; Chougnet, C.; Schito, M.; Near, K. A.; Shearer, G. M.; Li, C.; Langhorne, J.; Sher, A., "Malaria Infection Induces Virus Expression in Human Immunodeficiency Virus Transgenic Mice by CD4 T Cell-Dependent Immune Activation," *J. Infectious Diseases,* 2001, 183, 1260–1268.

Tuberculosis (Mtb) remains today one of the most infectious diseases in the world. It is estimated that one-third of the world's population is infected by the tubercular organism, which claims the lives of 2–3 million people each year. In the large majority of those infected the infection remains latent, with only 10 percent ever developing active tuberculosis. The organism, however, is opportunistic and emerges to strike those with weakened immune systems, such as the elderly, AIDS patients, and people suffering from malnutrition. The infecting organism is a rod-shaped bacterium known as *Mycobacterium tuberculosis*.

Because relatively few drugs have been found satisfactory for the treatment of tuberculosis the occurrence of drug resistant tubercular *bacilli* looms with a frightening potential. Bacterial resistance to each of the presently available antituberculosis drugs has been observed, even with their combined use. The combined use of treatments involving rifampin and pyrazinamide has been shown to be potentially lethal. See, *Morbidity and Mortality Weekly Reports* 2001, 50, 289–291.

Once ranked among the most common causes of death, improved methods of prevention, detection, diagnosis, and treatment have greatly reduced the number of people who get tuberculosis and the number of people who die from this disease. In the last ten years, however, tuberculosis has re-emerged as a major concern. That is, after decades of steady decline there has been resurgence in the number of new cases. Reports have appeared concerning clusters of the disease, especially the more dangerous multidrug-resistant (MDR-TB) forms, occurring in several hospitals and prisons. The complication of multi-drug resistance constitutes one of the major causes of therapeutic failure. See, Hutton, M. D., Stead, W. W., Cauthen, G. M., et al., "Nosocomial Transmission of Tuberculosis Associated With a Draining Abscess," *J. Infect. Dis.*, 1990, 161, 286–295; Selwyn, P. A., "Tuberculosis in the AIDS Era: a New Threat From an Old Disease," N.Y. *J. Med.*, 1991, 91, 233–235; Selwyn, P. A., Hartel, D., Lewis, V. A., et al., "A Prospective Study of the Risk of Tuberculosis Among Intravenous Drug Users With Human Immunodeficiency Virus Infection," *New England J. Med.*, 1989, 320, 545–550; Starke, J. R., "Prevention of Tuberculosis," *Seminars in Respiratory Infections*, 1989, 4 (4), 318–325. This raises the specter of a serious accelerating public health problem with the potential to spread regionally and nationally. In 1953, there were 84,304 reported cases of TB. See, Bloch, A. B., Rieder, H. L. and Kelly, G. D., The Epidemiology of Tuberculosis in the United States, *Seminars in Respiratory Infections*, 1989, 4(3), 157–170. For the next 31 years the number of new cases evidenced a steady downward drift. By 1984 the number of new incidences each year had declined 74 percent. The downward trend then reversed. During the 1980's, outbreaks of tuberculosis began to increase in the United States, partly as a result of the spread of AIDS. The disease also struck growing numbers of homeless people and drug addicts. By the late 1980's, 25,000 new cases were being reported annually, with about 2,000 deaths from the disease. By 1992, instances of the disease had increased 20 percent over the number of cases in 1985.

AIDS has been an important factor in the resurgence of tuberculosis. TB is one of the most common opportunistic infections of AIDS, and is the AIDS-defining condition in about 30 percent of AIDS cases. See, Harries, A. D., Tuberculosis and Human Immunodeficiency Virus Infection in Developing Countries," *Lancet*, 1990, 335, 387–390. Over the next decade this could lead to a dramatic increase in the number of deaths from TB in places where TB and AIDS are endemic. According to the World Health Organization (WHO), 4 million people worldwide are infected with both the tubercular bacillus and HIV. See, Raviglione, M. C., Narain, J. P., and Kocchi, A., "HIV-associated Tuberculosis in Developing Countries: Clinical Features, Diagnosis, and Treatment," *Bulletin of the International Union Against Tuberculosis Lung Disease*, 1992, 70 (4), 515–526. Treating TB in patients with HIV has added complexities. Coexisting infections and other AIDS-associated disorders require treatments that may interact with the antibiotics used to treat TB. High rates of toxicity and drug reactions, especially with rifampin, have been reported in TB patients with AIDS. See, FitzGerald, J. M., Grzybowski, S., and Allen, E. A., "The Impact of Human Immunodeficiency Virus Infection on Tuberculosis And its Control," *Chest*, 1991, 100 (1), 191–200; Nolan, C. M., "Failure of Therapy for Tuberculosis in Human Immunodeficiency Virus Infection," *Am. J. Med. Sc.*, 1992, 304 (3), 168–173; Small, P. M., Schecter, G. F., Goodman, P. C., et al., "Treatment of Tuberculosis in Patients With Advanced Human Immunodeficiency Virus Infection," *New England J. Med.*, 1991, 324, 289–294. Another complicating factor is that the various extrapulmonary types of TB appear to be more common among patients with HIV. See, Fischl, M. A., Daikos, G. L., Uttamchandani, R. B., et al., "Clinical Presentation And Outcome Of Patients With HIV Infection And Tuberculosis Caused By Multi-Drug Resistant *Bacilli,*" *Ann. Int. Med.*, 1992, 117, 184–190; Pitchenik, A. E., and Fertel, D., "Tuberculosis and Nontuberculosis Mycobacterial Disease," *Med. Clin. N. Am.*, 1992, 76 (1), 121–171. The risk of developing tuberculosis among HIV positive patients is over 100 times higher than among HIV negative individuals. Tuberculosis is a unique, serious disease. Unlike other diseases associated with AIDS, it may be spread by airborne transmission to adults and children who are not at risk of AIDS. In 1992, worldwide tuberculosis mortality was two million, in addition to the report of 8 million new cases.

Resistance to current antituberculosis therapy is another threatening problem. Multi-drug-resistant strains of *M. tuberculosis*, resistant to as many as nine drugs, are 50–80% fatal even with intensive treatment. In the U.S., drug-resistant strains have been identified in seventeen states since 1989. Isoniazid resistance in the U.S. is present in 5.3% and secondary resistance in 19.4% of isolates, while the figures for rifampin are 0.6% and 3.2%, respectively. The resurgence of drug-resistant-tuberculosis has initiated a renewal of interest in a strategic search for new prototype leads. The oceans, with their unique and wide range of biodiversity, generating chemically diverse metabolites, emerge as an outstanding resource for new agents with anti-Mycobacterial activity. See, El Sayed, K. A.; Bartyzel, P.; Shen, X.; Perry, T. P.; Zjawiony, J. K.; and M. T. Hamann, "Marine Natural Products as Antituberculosis agents." *Tetrahedron* 2000, 56, 949–953.

Presently available antimalarial drugs include the quinoline derivative quinine and its (+) diastereoisomer (with respect to the asterisked carbon), quinidine (see Formula I below), which are natural quinoline alkaloids obtained from Cinchona bark. They are effective blood schizonticidal agents active against all four species of malaria parasites (*Plasmodium falciparum, P. vivax, P. ovale* and *P. malaria*). They are also gametocidal for all species except *P. falciparum*. Their mechanism of action was thought to be by intercalation into parasite DNA, thus inhibiting DNA and RNA synthesis. Now it is believed that the activity is due to complexation with malarial pigment. Plasmodia derive essential amino acids from the degradation of host erythrocyte hemoglobin. Since ferritoprotoporphyrins (a hemoglobin degradation product) are toxic to membranes, the parasite sequesters these products as hemazoin (the malarial pigment). Quinine forms a complex with ferritoprotoporphyrin IX; preventing hemazoin sequestration and resulting in cell lysis. Quinine also affects mammalian lysosomes causing significant adverse effects. See, Angerhofer, C. K.; Konig, G. M.; Wright, A. D.; Sticher, O.; Milhous, W. K.; Cordell, G. A.; Farnsworth, N. R.; Pezzuto, J. M. 1992 In: Advances in Natural Product Chemistry, pp311–329. ed. by Atta-ur-Rahman. Harwood Academic Publishers, Gmbh, Chur.; Stahl, P.; Schwartz, A. L. *J. Clin. Invest.* 1986, 77, 657; c. Chaw, M.; Panosian, C. B. *Clinical Microbiology Rev.*, 1995, 8, 427.

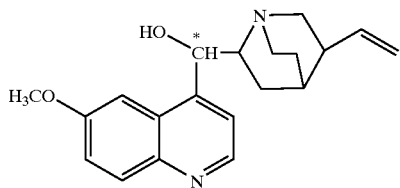

(-) - Quinine
(+) - Quinidine

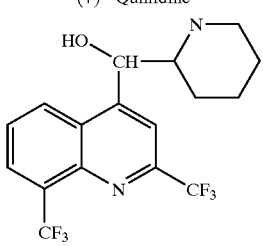

Mefloquine

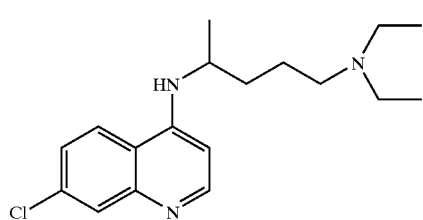

Chloroquine

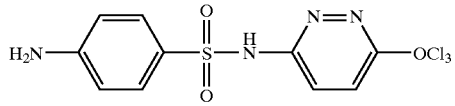

Sulfadoxine

Sulfadoxine (see Formula II above) is a sulfonamide. It is a blood schizonticide drug active against *P. falciparum* and less active against *P. vivax*. The only sulfone in use as a treatment for malaria is dapsone (see Formula III below) and it is similar in activity to sulfadoxine. Dapsone provides solid precedence for the potential of a clinically useful drug to exhibit activity against both *Plasmodium* and *Mycobacterium*.

The discovery of endoperoxides as a new class of antimalarial agents began with the prototype artemisinin (see Formula IV below). Artemisinin was first isolated from an ancient Chinese herbal remedy. See, Klayman, D. L., *Science*, 1985, 228, 1049; Hien, T. T.; White, N. J., *Lancet*, 1993, 341, 603. Several semisynthetic derivatives including artemether, arteether and artesunate (see Formula V below) and the synthetic derivative arteflene (see Formula VI below), are already in development or are used clinically. See, Asawamahasakda, W.; Ittarat, I.; Pu, Y. M.; Ziffer, H.; Meshnick, S. R., *Antimicrob. Agents Chemother.* 1994, 38, 1854; Bradley, D. J., *Trop. Med. Parasitol.* 1994, 45, 259. Arteether has proven useful in high-risk malaria patients, including those with cerebral malaria. The endoperoxide moiety is necessary for antimalarial activity, since analogs that lack this group are inactive. See, Brossi, A.; Venugopaplan, B.; Gerpe, L. D.; Yeh, H. J. C.; Flippen-Anderson, J. L.; Luo, X. D.; Milhouse, W.; Peters, W., *J. Med. Chem.* 1988, 31, 645. b. "China Cooperative Research group on Qinghaosu and Its Derivatives as Antimalarials," 1982, *J. Traditional Med.* 2, 3. The endoperoxide moiety may explain the selective toxicity to the malarial parasite, since the parasite is rich in iron and heme, which catalyze the reductive cleavage of the endoperoxide bridge, generating free radicals and other electrophilic intermediates, which in turn act as alkylating agents for specific malaria proteins. See, Meshnick, S. R.; Yang Y. -Z.; Lima, V.; Kuypers, F.; Kamchon-wongpaisan, S.; Yuthavong, Y., *Antimicrob. Agents. Chemother,* 1993, 37, 1108; Posner, G. H.; C. H., Oh.; Wang D.; Gerena L.; Milhouse W.; Meshnick W.; Asawamahasakda W., *J. Med. Chem.,* 1994, 37, 1256. This process has been demonstrated in vitro in model systems and in intact parasites. Despite the clinical observation that endoperoxides are free of toxicity, evidence has been presented that some of the first generation artemisinin derivatives are neurotoxic in multidose laboratory studies. See, Brewer, T. G. *Am. J. Trop. Med. Hyg.,* 1994, 51, 251. The origin of neurotoxicity is still under investigation; however the endoperoxide antimalarials are likely to become acceptable candidates replacing the traditional antimalarials, such as chloroquine (see Formula VII above) for which resistance is widespread.

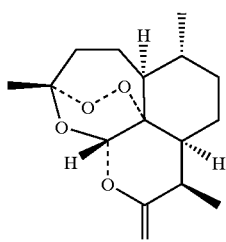

Artemisinin

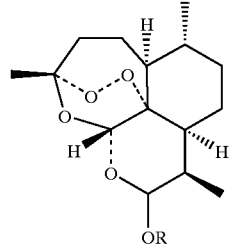

| Artemisinin derivatives: | R |
|---|---|
| Dihydroartemisinin | H |
| Artemether | CH$_3$ |
| Arteether | —CH$_2$CH$_3$ |
| Artesunate | —COCH$_2$CH$_2$COONa |

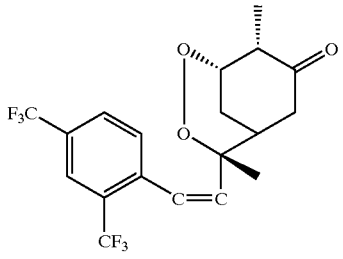

Arteflene (III)

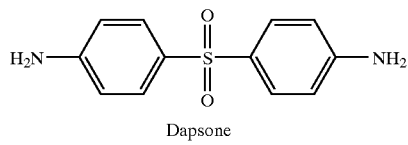

Dapsone

Current antituberculosis drugs are divisible into First-Line agents and Second-Line agents. First-line agents include the following:

1) Isoniazid (INH): (see Formula VIII below) The apparent mechanism of action of this synthetic isonicotinic acid derivative is the inhibition of mycolic acid synthesis. See, Sacchettini; J. C., Blunchard, J. S., The Structure and Function of the Isoniazid Target in *Mycobacterium tuberculosis*, Res. Microbiol. 1996, 147, 36–43. Mycolic acid is a peculiar, integral, structural component of Mycobacteria. INH is also reported to combine with catalase/peroxidase, an enzyme that is unique to isoniazid-sensitive strains of Mycobacteria, and results in the disorganization of cell metabolism. In response to INH treatment, saturated hexacosanoic (C26:0) was found to accumulate on a 12-kilodalton-acyl carrier protein (AcpM) that normally carried mycolic acid precursors. See, Mdluli, K.; Slayden, R. A.; Zhu, Y.; Ramaswamy, S.; Pan, X.; Mead, D.; Crane, D. D.; Musser, J. M.; Barry C. E. III, Inhibition of a *Mycobacterium tuberculosis* β-ketoacyl ACP Synthase by Isoniazid, Science. 1998, 280, 1607–1610. Amino acid-altering mutations in the KasA protein were identified in INH-resistant patient isolates that lacked other mutations associated with resistance to this drug. Resistance can occur due to the lack of catalase activity and reduced drug penetration. See, Smith, C. M.; A. M. Reynard, Treatment of Tuberculosis, In Essentials of Pharmacology, W. B. Saunders Company: Philadelphia, 1995, p 395–403.

(VIII)

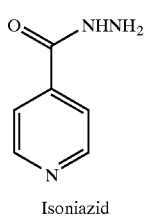

Isoniazid (IX)

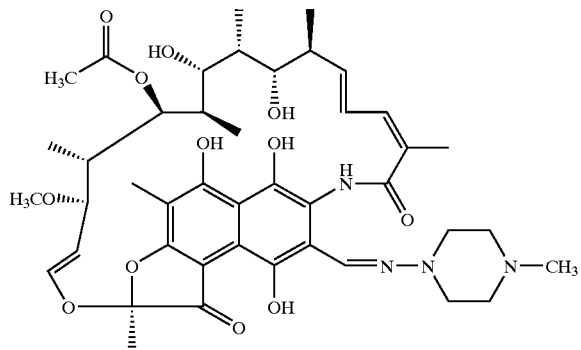

Rifampin (X)

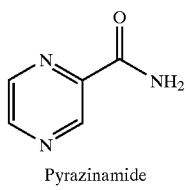

Pyrazinamide (XI)

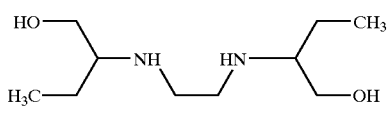

Ethambutol (XII)

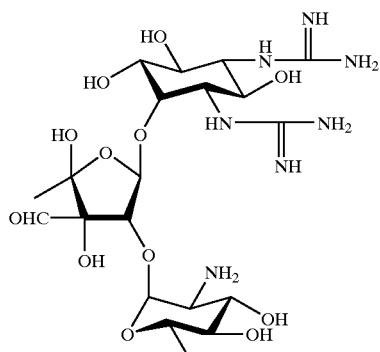

Streptomycin (XIII)

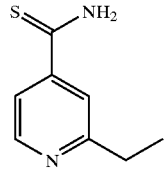

Ethionamide

2) Rifampin (see Formula IX above) is a mycobactericidal and bactericidal semisynthetic derivative of rifamycin B which inhibits DNA-dependent RNA polymerase in prokaryotic, but not in eukaryotic, cells. Rifampin enters phagocytic cells and can kill intracellular, intracavitary or even dormant tuberculosis bacilli. See, Riepersberg, W. Molecular Biology, Biochemistry, and Fermentation of Aminoglycoside Antibiotics, Biotechnology of Antibiotics, 2nd Edition, Revised and Expanded, Strohl, W. R. Marcel Decker, New York, Basel, Hong Kong, 1997, p 81–163. Resistance to rifampin can occur rapidly and as a result this drug should never be administered alone.

3) Pyrazinamide (see Formula X above) is an analog of nicotinamide which is now recognized as an important first line agent in tuberculosis therapy. It is only active against intracellular organisms in macrophages at acidic pH. After phagocytosis, the organisms are contained in phagolysosomes of low pH. Pyrazinamide is usually used in combination with other drugs. See, Rang, H. P., M. M. Dale, J. M. Ritter, and P. Gardner, Antimycobacterial Agents. In Pharmacology (3rd Ed.) Churchill Livingstone, N.Y. 1995, p 738–743.

4) Ethambutol (see Formula XI above) is an ideal example of the discovery of antituberculosis agents by the in vitro screening of compounds for such activity. It is a synthetic tuberculostatic compound that acts by interfering with mycolic acid with an ill-defined mechanism. The (+) isomer is the only active form of ethambutol and it develops resistance like most other antituberculosis agents when used independently.

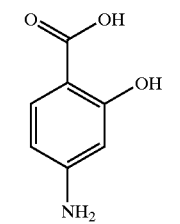

p-Aminosalicylic acid (XIV)

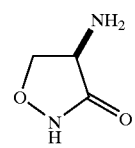

D-Cycloserine (XV)

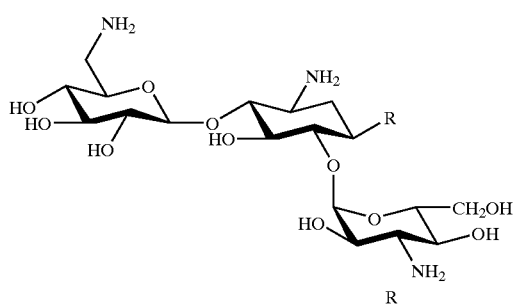

Kanamycin A (XVI)

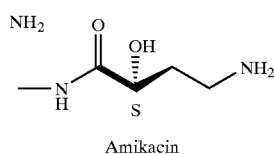

Amikacin (XVII)

5) Streptomycin (see Formula XII above) is an aminoglycoside-antibiotic. Streptomycin was the first drug available for tuberculosis but it is now the least used of the first line drugs due to its high toxicity and the rapid emergence of resistance. It is bactericidal against all Mycobacterial forms. See, Riepersberg, W. Molecular Biology, Biochemistry, and Fermentation of Aminoglycoside Antibiotics, Biotechnology of Antibiotics, 2nd Edition, Revised and Expanded. Strohl, W. R. Marcel Decker, New York, Basel, Hong Kong, 1997, p 81–163; Rost, W. J. Chemistry of the Amino Glycosides: Structure/Function Relationships, and Dworzack, D. L. Aminoglycosides: Mechanisms of Action and Resistance In: The Aminoglycoside Antibiotics: A Guide to Therapy. Barnes, W. G.; Hodges. G. R., Eds. CRC Press, Boca Raton, Fla. 1984, pp 5–22 and 23–44.

Second-Line Anti-Tuberculosis Drugs Include the Following:

1) Ethionamide (see Formula XIII above) is a synthetic congener of isonicotinic acid with bacteriostatic activity against *M. tuberculosis*. Ethionamide must be used in combination with other drugs. The gastrointestinal and neuropathic side effects of this material have limited the use of ethionamide.

2) p-Aminosalicylic acid (see Formula XIV above) is a synthetic bacteriostatic agent that inhibits mycobacterial growth by altering folate metabolism. It is used in the developing world, despite its toxicity, for economic reasons.

3) D-Cycloserine (see Formula XV above) is a broad-spectrum, pH-sensitive antibiotic. D-cycloserine's homology with D-alanine illustrates its competitive inhibitory activity of cell wall synthesis by preventing the formation of both D-alanine and D-alanine-D-alanine dipeptide which is added to the initial tripeptide side-chain on N-acetylmuramic acid. This prevents completion of a major block of peptidoglycan. The adverse central nervous system (CNS) effects of cycloserine restrict its application.

4) The aminoglycosides kanamycin A (see Formula XVI above), amikacin (see Formula XVII above) and peptide antibiotics; capreomycins (see Formula XVIII below), and tuberactinomycins (Viomycins) (see Formula XIX below): Cross-resistance, expense and risk of renal and ototoxicity have restricted the application of aminoglycosides and peptides as antituberculosis drugs.

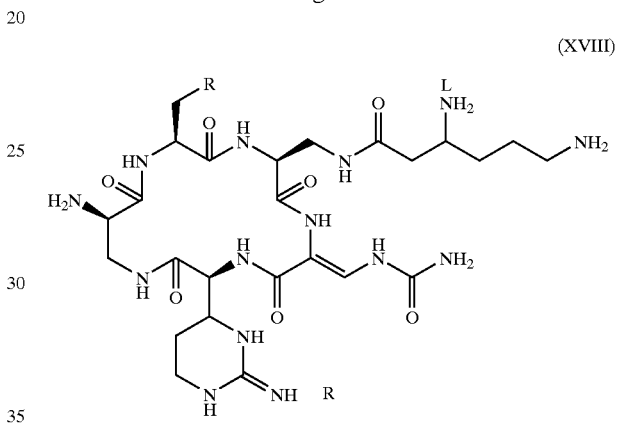

Capreomycin IA OH
Capreomycin IB H (XVIII)

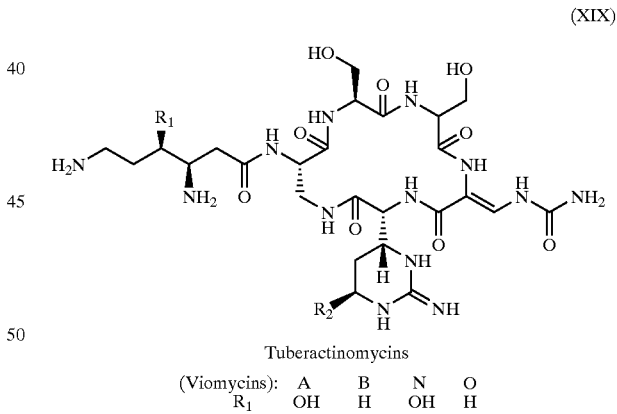

Tuberactinomycins

| (Viomycins): | A | B | N | O |
|---|---|---|---|---|
| $R_1$ | OH | H | OH | H |
| $R_2$ | OH | OH | H | H |

(XIX)

5) Ciprofloxacin and Ofloxacin are synthetic quinolones used as primary drugs in the presence of resistance to both isoniazid and rifampin. See, Ulubelen, A.; Evren, N.; Tuzlaci, E. Johansson, C. Diterpenoids from the Roots of *Salvia hypargeia*, J. Nat. Prod. 1988, 51, 1178–1183. The wide use of quinolones may also create resistance.

It is estimated that 1 in 100,000 to 1 in 100 million *bacilli* are initially resistant to any single drug used against TB. See U.S. Congress, Office of Technology Assessment, "The Continuing Challenge of Tuberculosis" OTA-H-574, Washington, D.C., U.S. Government Printing Office, September, 1993, p. 75. To combat this, the use of combination chemotherapy to treat TB has been standard practice. Initially INH, SM, and PAS are given, followed with INH, SM, and EMB, then INH and RIF. See, Simone, P. M., and Iseman, M. D., "Drug-resistant Tuberculosis: a Deadly—and Growing—Danger," *J. Resp. Dis.*, 1992, 13 (7), 960–971; U.S. Dept. of Health and Human Services, PHS, Centers for Disease Control and Prevention, "Initial Therapy for Tuberculosis in the Era of Multidrug Resistance, recommendations of the Advisory Council for the Elimination of Tuberculosis," *Morbidity and Mortality Weekly Report,* 1992, 42 (RR-7), 1–8; Villarino, M. E., Geiter, I. J., and Simone, P. M., "The Multidrug Resistant Tuberculosis Challenge to Public Health Efforts to Control Tuberculosis," *Public Health Reports,* 1992, 107 (6), 616–625. Such a multidrug procedure is estimated to be adequate for over 95 percent of TB patients. See, Bloch, A. B., Medical Officer, Surveillance and Epidemiology Branch, Division of Tuberculosis Elimination, Centers for Disease Control and Prevention, PHS, U.S. Health and Human Services, Atlanta, Ga., notes from the Advisory Committee for the Elimination of Tuberculosis Meeting, 1992. The remaining 4 to 5 percent are resistant to 2 or more drugs, and cases of resistance to as many as 11 drugs have been documented. See Goble, M., Iseman, M. D., Madsen, L. A., et al., "Treatment of 171 Patients With Pulmonary Tuberculosis Resistant to Isoniazid and Rifampin," *New England J. Med.,* 1993, 328 (8), 527–532.

Outbreaks of drug-resistant TB are not entirely new, (see, Reeves, R., Blakey, D., Snider, S. E., et al., "Transmission of Multiple Drug Resistant TB: Report of a School and Community Outbreak," *Am. J. Epidem.,* 1981, 113, 423–435; U.S. Dept. of Health and Human Services, PHS, Centers for Disease Control and Prevention, "Outbreak of Multidrug Resistant Tuberculosis—Texas, California, and Pennsylvania," *Morbidity and Mortality Weekly Report,* 1990, 32 (40), 521–523) but such outbreaks have become more common, larger in scope, and more dangerous. Since 1990 there have been at least 9 outbreaks of MDR-TB in the United States, (see, U.S. Dept. of Health and Human Services, PHS, Centers for Disease Control and Prevention, "Program Briefing, 1992: Tuberculosis Elimination," U.S. Dept. of Health and Human Services, Atlanta, Ga., unpublished report, Mar. 9, 1993) with at least seven others reported but not investigated. Most, although not all, individuals who developed active MDR-TB in these outbreaks were HIV-seropositive. The majority (79 to 89 percent) of the individuals affected by these outbreaks died from the disease and have included health care workers and prison guards. According to a press release from the World Health Organization (WHO), the incidence of drug-resistant Mtb has dramatically increased worldwide. According to the NIAID, *M. tuberculosis* strains resistant to two or more first-line drugs have been detected in more than 100 countries and territories. See, "Reuters Medical News" ® http://id.medscape.com/reuters/prof/2000/03/03.24/pb03240a.html. This rising prevalence of MDR-Mtb and the complexities of treating Mtb in patients with HIV have heightened the need for new anti-Mtb drugs.

Secondary metabolites isolated from natural sources, predominantly microorganisms and plants, have provided mankind with many of the therapeutic agents currently on the market. These natural products have been used directly as drugs, or have provided leads for the-synthetic preparation of pharmaceutical products. Currently, 37% of sales in the pharmaceutical industry come from products derived from natural sources. See, Joffe, S. and Thomas, R., *Ag. Biotech. News Inform.* 1989, 1, 697. Approximately 60% of those compounds commercially available or in the late stages of clinical trials for the treatment of infectious diseases or cancer are of natural product origin. See, Cragg, G. M.; Newman, D. J.; Snader, K. M. "Natural Products in Drug Discovery and Development" *J. Nat. Prod.* 1997, 60, 52–60. In recent years, a small group of researchers have isolated over 12,000 novel compounds from marine invertebrates, algae, and microorganisms. See, Faulkner, D. J., *Nat. Prod. Reps.* 1992, 9, 323, (And previous reports in this series) Over a dozen of these compounds (aplidine, aplyronine, dolastatin 10, bryostatin, ecteinascidin 743, kahalalide F, halichondrin B, lamellarine N, sarcodictyins, thiocaroaline, spongistatins, etc.) are in early clinical or late preclinical development. See, Shu, Y. "Recent Natural Products Based Drug Development: A Pharmaceutical Industry Perspective" 1998, 61, 1053–1071, Urban, S.; Hickford, S. J. H.; Blunt, J. W.; Munro, M. H. G.; Kelly, M. "Bioactive Marine Alkaloids," Current *Org. Chem.* 2000, 4, 765–807.

BRIEF SUMMARY OF THE INVENTION

A class of sponge-derived alkaloids known as the "manzamines" show improved activity against malaria in mice over both chloroquine and artemisinin. The significant improvement in potency of the manzamines over the clinically used drugs in malaria-infected animals is due in part to an unexpected immunostimulatory response. The manzamines have also shown significant activity in vitro against *Mycobacterium tuberculosis* and *Toxoplasma gondii*. Manzamines have not previously been reported, however, to play a role in the treatment of infectious and parasitic diseases.

It has been found that the sponge-derived manzamines, as well as derivatives and analogs thereof are useful in the treatment of infectious diseases. Manzamines, manzamine derivatives and manzamine analogs are useful as antiparasitics, antimicrobials (bacteriology) and antivirals and are suitable against opportunistic infections (mycology). The present invention also relates to the following three novel manzamines:

1. ent(−) 8-hydroxymanzamine A;
2. manzamine dimer (new-kauluamine); and
3. ent-manzamine F.

DETAILED DISCLOSURE OF THE INVENTION

The manzamines are complex, polycyclic, marine-derived alkaloids first reported by Higa and coworkers in 1986 from the Okinawan sponge genus *Haliclona*. See, Sakai, R.; Higa, T.; Jefford, C. W.; Bernardinelli, G. "Manzamine A; An Antitumor Alkaloid From a Sponge," *J. Am. Chem. Soc.* 1986, 108, 6404–6405. These compounds possess a fused and bridged tetra- or pentacyclic ring system that is attached to a β-carboline moiety. Since the first report of manzamine A, an additional thirty manzamine-type alkaloids have been reported from the sponge genera *Prianos*, (see, Ohtani, I. I.; Ichiba, T.; Isobe, M.; Kelly-Borges, M.; Scheuer, P. J. "Kauluamine: An Unprecedented Manzamine Dimer from an Indonesian Marine Sponge, *Prianos* sp. *J. Am. Chem. Soc.* 1995, 117, 10743–10744), *Haliclona*, (see, Sakai, R.; Kohmoto, S.; Higa, T.; Jefford, C. W.; Bernardinelli, G. "Manzamines B & C, Alkaloids From a Sponge, *Haliclona* sp. *Tetrahedron Lett.* 1987, 28, 5493–5496; Higa, T.; Sakai, R.; Kohomoto, S.; Lui, M. S., "Antitumor alkaloids from marine sponges," Eur. *Pat. Appl.* 1987, EP 87-310872871210; Kobayashi, M.; Chen, Y. J.; Aoki, S.; In, Y.; Ishida, T.; Kitagawa, I. *Tetrahedron* 1995, 51, 3727–3736), *Xestospongia*, (see, Ichiba, T.; Sakai, R.; Kohomoto, S.; Saucy, G.; Higa, T. "New Manzamine Alkaloids From A Sponge Of The Genus *Xestospongia*," *Tetrahedron Lett.* 1988, 29, 3083–3086; Edrada, R. A.; Proksch, P.; Wray, V.; Witte, L.; Muller, W. E. G.; Van Soest, R. W. M., *J. Nat. Prod.* 1996, 59, 1056–1060), *Pachypellina*, (see, Ichiba, T.; Corgiat, J. M.; Scheuer, P. J.; Kelly-Borges, M. "8-Hydroxymanzamine A, A β-carboline Alkaloid From a Sponge, *Pachypellina* sp.," *J. Nat. Prod.* 1994, 57, 168–170), *Petrosia*, (see, Crews, P.; Cheng, X. C.; Adamczeski, M.; Rodriguez, J.; Jaspars, M.; Schmitz, F. J.; Traeger, S. C.; Prodesimo, E. O., "1,2,3,4-Tetrahydro-8-hydroxymanzamines, Alkaloids From Two Different Haplosclerid Sponges," *Tetrahedron* 1994, 50, 13567–13574), *Cribrochalina, Ircinia*, (see, Kondo, K.; Shigemori, H.; Kikuchi, Y.; Ishibashi, M.; Sasaki, T.; Kobayashi, J. "Ircinals A and B From the Okinawan Marine Sponge *Ircinia* sp.: Plausible Biogenetic Precursors of Manzamine Alkaloids," *J. Org. Chem.* 1992, 57, 2480–2483), *Amphimedon* (see, Tsuda, M.; Kawasaki, N.; Kobayashi, J., "Ircinols A and B, First Antipodes of Manzamine-Related Alkaloids from an Okinawan Marine Sponge," *Tetrahedron* 1994, 50, 7957–7960; Tsuda, M.; Kawasaki, N.; Kobayashi, J. "Keramaphidin C and Keramamine C, Plausible Biogenetic Precursors of Manzamine C from an Okinawan Marine Sponge," *Tetrahedron Lett.* 1994, 35, 4387–4388; Kobayashi, J.; Tsuda, M.; Kawasaki, N.; Matsumoto, K; Adachi, T. "Keramaphidin B, a Novel Pentacyclic Alkaloid From a Marine Sponge *Amphimedon* sp.: A Plausible Biogenetic Precursor of Manzamine Alkaloids," *Tetrahedron Lett.* 1994, 35, 4383–4386; Tsuda, M.; Inaba, K.; Kawasaki, N.; Honma, K.; Kobayashi, J. "Chiral Resolution of ±keramaphidin B and Isolation of Manzamine L, a New β-Carboline Alkaloid From a Sponge *Amphimedon* sp.," *Tetrahedron* 1996, 52, 2319–2924; Kobayashi, J.; Watanabe, D.; Kawasaki, N.; Tsuda, M. *J. Org. Chem.* 1997, 62, 9236–9239; Tsuda, M.; Watanabe, D.; Kobayashi, J., "Ma'eganedin A, a New Manzamine Alkaloid from *Amphimedon* Sponge, *Tetrahedron Lett.* 1998, 39, 1207–1210) and *Pellina* (see, Nakamura, H.; Deng, S.; Kobayashi, J.; Ohizumi, Y.; Tomotake, Y.; Matsuzaki, T., "Keramamine-A and -B, Novel Antimicrobial Alkaloids from the Okinawan Marine Sponge *Pellina* sp., "*Tetrahedron Lett.* 1987, 28, 621–624).

The isolation of the manzamine alkaloids from a diversity of unrelated species provides strong evidence for a microbial origin for the metabolites. Re-examination of the sponges identified as Prianos and Pachypellina in earlier publications has confirmed that these are members of the same genus as the sponge studied herein, but differ at the species level. This new genus with at least four species is relatively common in Indonesia, The Philippines, Micronesia, and northern Papua New Guinea, down to −60 m. Manzamines exhibit a diverse range of bioactivities against infectious organisms including antibacterial, antimycobacterial, cytotoxicity and the exciting and highly encouraging curative activity against malaria in animal models.

The Diversity of Reported Manzamine Producing Sponges

| Orders | Family | Genus |
|---|---|---|
| Halichondrida | Halichondriidae | Prianos |
| Haplosclerida | Chalinidae | Haliclona |
| | Niphatidae | Amphimedon |
| | | Cribrochalina |
| Petrosida | Petrosiidae | Petrosia |
| | | Xestospongia |
| | Oceanapiidae | Pellina |
| | | Pachypellina |
| Dictyoceratida | Irciniidae | Ircinia |

Manzamines and compositions containing them can be administered via any suitable therapeutic method and technique presently or prospectively known to those skilled in the art. Further, the compounds for use in this invention have use as starting materials for the preparation of other useful compounds and compositions.

Skilled chemists having the benefit of the present disclosure of the structure of these manzamines can readily use procedures to prepare the subject compounds from sponge/microbial extracts or through synthetic or biocatalytic transformations. In carrying out such operations, suitable filtration, chromatographic, crystallization and other purification techniques well known in the art may be used. These techniques may include, for example, reversed phase (RPLC), column, vacuum flash, medium pressure (MPLC) and high performance liquid chromatography (HPLC) with a suitable column such as silica gel, Sephadex LH-20, ammonia-treated silica gel, bonded phase RP-18, RP-8 and amino columns. Such columns are eluted with suitable solvents such as hexanes, ethyl acetate, acetone, methylene chloride, methanol, isopropanol, acetonitrile, water, trifluoroacetic acid (TFA) and various combinations thereof.

The dosage administered to a host will be dependent upon the identity of the infection, the type of host involved, its age, weight, health, kind of concurrent treatment, if any, frequency of treatment and therapeutic ration.

The compounds of the subject invention can be formulated according to known methods for preparing pharmaceutically useful compositions. Formulations are described in detail in a number of sources that are well known and readily available to those skilled in the art. For example, *Remington's Pharmaceutical Science* by E. W. Martin describes formulations that can be used in connection with the subject invention. In general, the compositions of the subject invention will be formulated such that an effective amount of the bioactive compound(s) is combined with a suitable carrier in order to facilitate effective administration of the composition.

In accordance with the invention, pharmaceutical compositions comprising, as the active ingredient, an effective amount of one or more of the subject compounds and one or more non-toxic, pharmaceutically acceptable carriers or diluents, can be used by persons of ordinary skill in the art. In addition, the pharmaceutical composition can comprise one or more of the manzamine compounds as a first active ingredient together with a second or third active ingredient comprising an antiinfective compound known in the art.

The most effective mode of administration and dosage regimen of manzamine compounds as antiinfective agents will depend upon the type of condition to be treated, the severity and course of that condition, previous therapy, the patient's health status and response to manzamines and the judgment of the treating physician. Manzamine compositions may be administered to the patient at one time or over a series of treatments.

The present pharmaceutical formulations comprise a manzamine or a manzamine derivative or analog or an optical isomer or racemate or tautomer thereof or a pharmaceutically acceptable salt thereof, optionally in admixture with a pharmaceutically acceptable diluent or carrier. Further, the invention relates to the treatment of infectious diseases or conditions which comprise administering to a subject suffering from or susceptible to such a disease or condition, a therapeutically effective amount of a manzamine, a manzamine derivative or analog, or an optical isomer or racemate or tautomer thereof or a pharmaceutically acceptable salt thereof.

Any of the identified manzamines and manzamine derivatives or analogs can be administered to an animal host, including a human patient, by itself, or in pharmaceutical compositions where it is mixed with suitable carriers or excipient(s) at doses therapeutically effective to treat or ameliorate a variety of infectious diseases. A therapeutically effective dose further refers to that amount of the compound sufficient to result in amelioration of symptoms associated with such disorders. Techniques for formulation and administration of the compounds of the instant application may be found in "Remington's Pharmaceutical Sciences", Mack Publishing Co., Easton, Pa., latest edition.

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art, especially in light of the detailed disclosure provided herein.

For any compound used in the method of the invention, the therapeutically effective dose can be estimated initially from cell culture assays. For example, a dose can be formulated in animal models to achieve a circulating concentration range that includes the IC50 (the dose where 50% of the cells show the desired effects) as determined in cell culture. Such information can be used to more accurately determine useful doses in humans.

A therapeutically effective dose refers to that amount of the compound that results in amelioration of symptoms or a prolongation of survival in a patient. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio between LD50 and ED50. Compounds which exhibit high therapeutic indices are preferred. The data obtained from these cell culture assays and animal studies can be used in formulating a range of dosage for use in human. The dosage of such compounds lies preferably within a range of circulating concentrations that include the ED50 with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in "The Pharmacological Basis of Therapeutics", Ch. 1 p1). Dosage amount and interval may be adjusted individually to provide plasma levels of the active moiety which are sufficient to maintain the desired effects.

In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated.

Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxy-methylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion.

Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example) as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. Naturally, the proportions of a co-solvent system may be varied considerably without destroying its solubility and toxicity characteristics. Furthermore, the identity of the co-solvent components may be varied.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agent. Various types of sustained-release materials have been established and are well known by those skilled in the art.

Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention may be provided as salts with pharmaceutically compatible counterions.

Pharmaceutically compatible salts may be formed with many acids, including but not limited to hydrochloric, sulfuric, acetic, lactic, tartaric, malic, succinic, etc. Salts tend to be more soluble in aqueous or other protonic solvents that are the corresponding free base forms.

Suitable routes of administration may, for example, include oral, rectal, transmucosal, transdermal, or intestinal administration; parenteral delivery, including intramuscular, subcutaneous, intramedullary injections, as well as intrathecal, direct intraventricular, intravenous, intraperitoneal, intranasal, or intraocular injections.

Alternately, one may administer the compound in a local rather than systemic manner, for example, via injection of the compound directly into an affected area, often in a depot or sustained release formulation.

Furthermore, one may administer the drug in a targeted drug delivery system, for example, in a liposome coated with an antibody specific for affected cells. The liposomes will be targeted to and taken up selectively by the cells.

The compounds of the subject invention can be used to treat a variety of infectious diseases in animals and humans including:

Antiparasitic

*Plasmodium falciparum* (Malaria)

*P. berghei*

*P. yoelli*

*P. chabaudi*

*Trypanosoma brucei* (Sleeping sickness)

*T. gambiense*

*T. rhodesiense*

*T. cruzi* (Chagas disease)

*T. colubriformis* (Filaria)

*Leishmania infantum* (Leishmania)

*L. donovani*

Nematodes

Antimicrobial/Bacteriology

*Enterococcus coli*

*E. faecalis*

*Bacillus subtilus*

*Staphylococcus aureus*

S. epidermidis
Pseudomonas aeruginosa
Trichophyton mentagrophytes
Streptococcus pyogenes
Salmonella sp.
Mycobacterium tuberculosis
M. intracellulare Opportunistic Infections (OI)/Mycology Candida albicans
C. tropicalis
C. kephyr
Cryptococcus neoformans
Aspergillus flavus
A. fumigatus
Microsporum canis
Trichophyton rubrum
T. mentagrophytes
T. quinckeanum
Cryptosporidium spp.
Toxoplasma gondii Antiviral HIV-1 (Human acquired immunodeficiency virus); HIV transmission inhibition
Herpesviruses (HSV-1, HSV-2, VZV, EBV, CMV, HHV-6, HHV-7, HHV-8)
Respiratory viruses (Flu A & B, RSV, PIV, MV, HRV, Ad)
Hepatitis B and C virus
Orthopoxyiruses (Vaccinia, Cowpox)
Special Pathogens: VEE, Punta Toro, Pichinde, Yellow fever, West Nile
Herpes viruses (HSV-1, HSV-2, HCMVSCID-hu, MCMV, GPCMV)
Respiratory viruses (Flu A & B, RSV, PIV-3, MV)
Hepatitis viruses (WHV, HDV, HBVtransgenic)
Orthopoxyiruses (Vaccinia, Cowpox)
Papillomaviruses (Shope, HPVSCID-hu)
Vesicular stomatitis virus (BHK/VSV)
Human rhinovirus (HRV)
Standard Operating Procedure
Isolation of Manzamine A and Ircinal A The following describes a quick, efficient and inexpensive method for the isolation of Manzamine A and Ircinal A from marine sponges collected in the Indo-Pacific.

Extraction

The manzamine-containing sponge (01 IND 035) can be processed either wet or dry. The extraction process begins with 4.5 kg of lyophilized sample (about 20 kgs wet wt). The sponge is extremely common and can be collected in Manado Bay, Sulawesi, Indonesia, from a depth ranging from −3 m to −40 m. It is irregularly massive with a rough surface. The texture is tough and crumbly. The colors in life are maroon (green underwater) externally and yellow internally. The skeleton is very irregular and composed of small round meshes set in irregular curving fascicles. The spicules are irregularly curved strongyles, $80^{-1}$ m. The sample represents an undescribed genus and species of the family Petrosiidae (Order Haplosclerida). This group of sponges is characterized by a skeletal architecture that is reminiscent of that of Xestospongia and Petrosia spp but is more irregular and fasciculate, by the presence of irregularly curved strongyles that range from 80–160 m, by a delicate fibrous texture, and by a mustard yellow internal coloration. A voucher specimen has been deposited at the Natural History Museum, London (BMNH 1997.11.11.9): Careful re-examination of specimens whose manzamine chemistry has been published, such as the Haliclona spp, Xestospongia spp, and Pellina sp., may reveal taxonomic congruence of these specimens, and thus a chemical marker for the genus group.

The dry or wet sponge can be extracted 4× with acetone. 16 liters of acetone is employed for each extraction. The acetone extracts are combined and evaporated to dryness under reduced pressure. The dry solid provides 215 g of crude manzamines from 4.5 kgs of dry sponge.

Chromatography

VACCUM FLASH CHROMATOGRAPHY WITH SILICA GEL: In order to reduce the amount of solvent required during column chromatography, VLC using silica gel, beginning with hexane and using increasing quantities of acetone, will remove oils and the majority of polar impurities.

VACCUM FLASH CHROMATOGRAPHY WITH REVERSED PHASE C18: In order to reduce the solvent required during column chromatography and to efficiently remove the sterols, methods are being developed to take advantage of the manzamines ability to elute from C18 with high concentrations of $H_2O$.

COLUMN CHROMATOGRAPHY: The crude extract (215 g) is subjected to column chromatography with a column (150 cm long, 13 cm diameter) with coarse frit, 6 kg silica gel (200–400 mesh) (Natland International Corporation; Catalog No. 80001–20, Phone: (919) 380-9775, Fax: (919) 380-9886, www.natland.com) and eluting first with hexane-acetone (95:5) 30 liters, hexane-acetone (90:10) 128 liters, hexane-acetone (85:15) 30 liters, hexane-acetone (70:30) 30 liters, hexane-acetone (50:50) 10 liters, hexane-acetone (50:50) 10 liters, acetone 6 liters, methanol-acetone (5:95) 10 liters, methanol-acetone (20:95) 4 liters and then methanol 10 liters. The solvent mixture is recovered by evaporating on a roto-evaporator and reutilized repeatedly. After evaporation to dryness, comparative TLC with standard manzamine A and ircinal A allows for simple process monitoring. The first three fractions (6 liters) elute with hexane-acetone (90:10) provide ircinal A (1.5 g) and can be monitored by $^1$H and $^{13}$C NMR spectra. The remaining fractions (122 liters) eluted with hexane-acetone (90:10) are found to contain manzamine A. These fractions are combined and weigh 15 g.

The manzamine A containing fraction (15 g) is then subjected to column chromatography by using a column (100 cm long, 6 cm diameter), 200 g alumina DCC (63–200 μm) and eluting with a mixture of hexane-acetone (85:15).

72 fractions of 500 ml each are collected, dried and checked by comparative TLC with manzamine A. Fractions 12–62 containing manzamine A are combined (11 g).

HPLC: The Manzamine A containing fraction (11 g) is subjected to RP-HPLC by using Phenomenex Luna C-8 15µ, 250×100.00 column with pre column Luna C-8 15µ, 50×50.00, and eluting isocratically with acetonitrile—water (3:7) at a flow rate of 20.00 ml per minute and monitoring with UV detector at 380 nm to obtained pure manzamine A (10 g).

Following this process the lipophilic extract of the undescribed Indo-Pacific Petrosiidae sponge (Order Haplosclerida) afforded the known manzamines A (0.66%), E (0.003%), J (0.0017%), and 6-deoxymanzamine X (0.0021%) along with the new compounds ent-8-hydroxymanzamine A (1.24%), ent-manzamine F (0.055%), and neo-kauluamine (0.0048%). A number of derivatives of these unusual alkaloids have been generated using microbial metabolism, synthetic and semisynthetic studies. Tables 1 and 2 show the in vitro Mtb and antimalarial activity of the natural, semisynthetic and metabolic products that have been isolated or prepared thus far. The three naturally occurring manzamines with endpoints of 1–3 µg/mL against Mtb clearly indicate that synthetic and metabolic modifications could easily lead to compounds with activity comparable to rifampin (a semisynthetic natural product in itself).

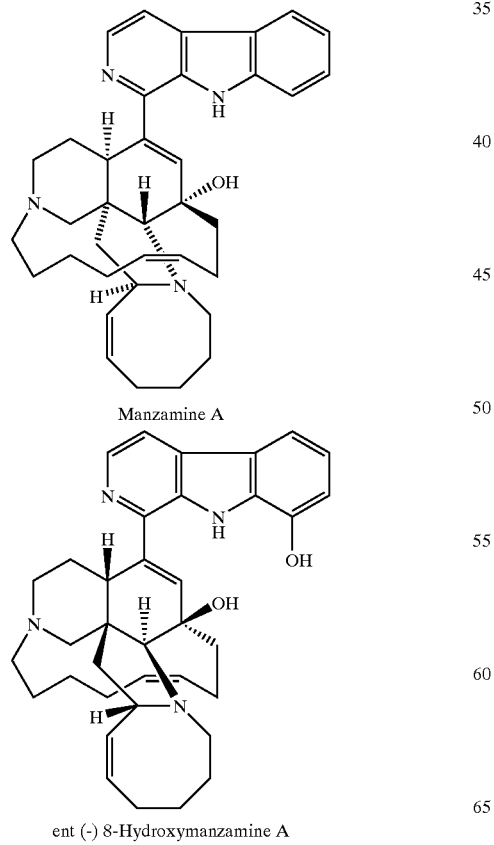

Manzamine A ent (-) 8-Hydroxymanzamine A

-continued

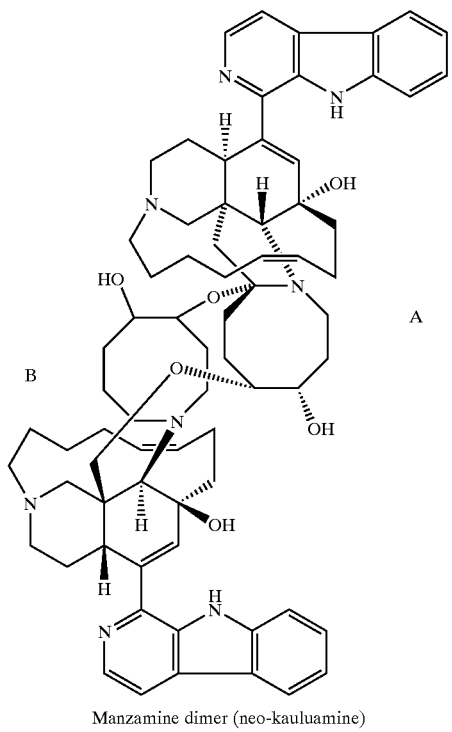

Manzamine dimer (neo-kauluamine)

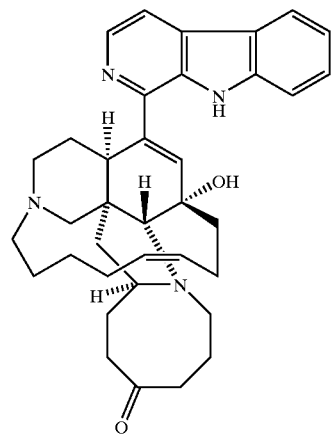

Manzamine E

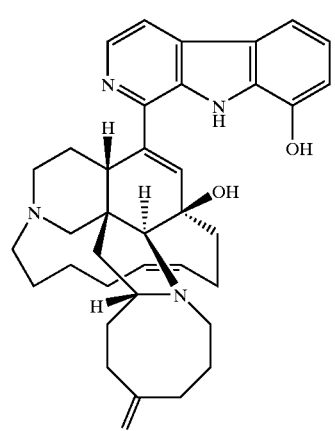

ent-Manzamine F

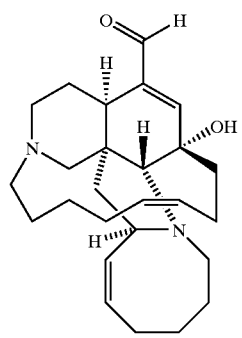
Ircinal A
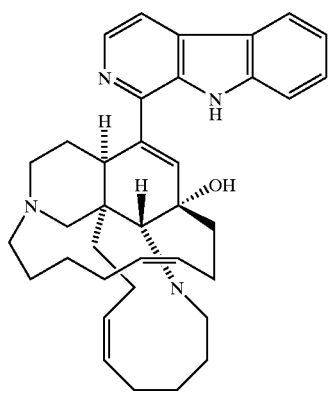
Manzamine J
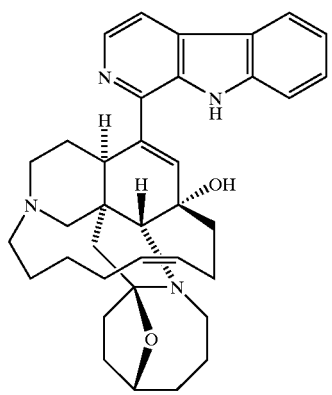
6-Deoxymanzamine X
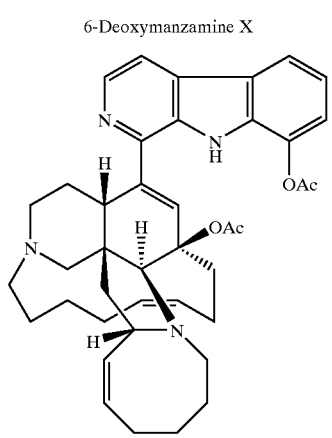
8-Hydroxymanzamine diAc
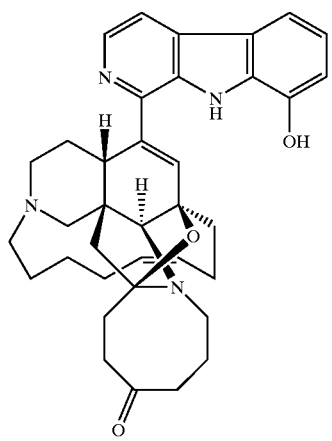
8-OHMA Metabolite 1
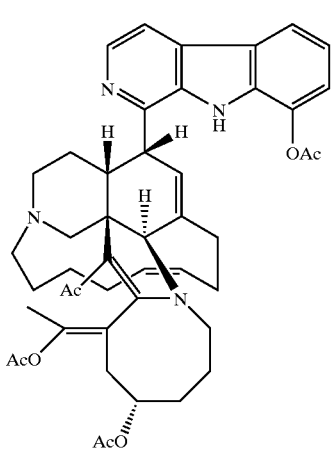
8-Hydroxymanzamine tetraAc
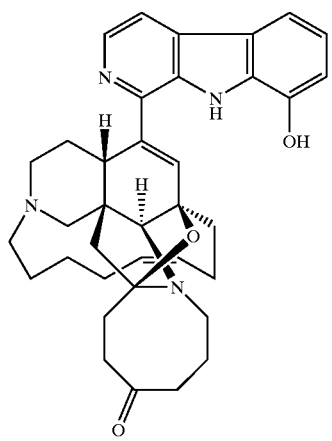
Mansamine L -continued

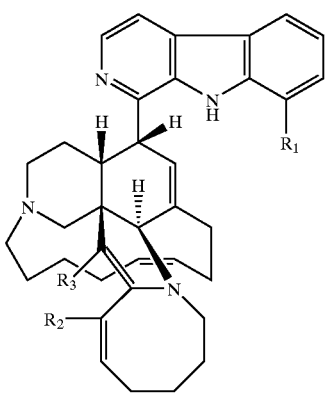

|  | R₁ | R₂ | R₃ |
|---|---|---|---|
| 8OHMA-Ac1 | OAc | Ac | Ac |
| 8OHMA-Ac2 | OAc | H | Ac |
| MA-Ac | H | H | Ac |

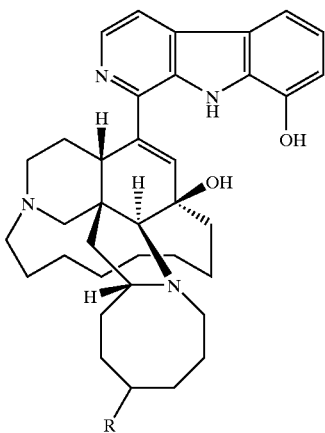

|  | R = |  |
|---|---|---|
| 8OHMA | H, | Tetrahydro |
| 8OHMA | α-OH, | Δ$^{15,16}$ |
| 8OHMA | β-OH, | Δ$^{15,16}$ |

Methods for obtaining these compounds are described in, for example, U.S. Pat. Nos. 4,895,852; 4,895,853; and 4,895,854; and International Patent Application number PCT/US00/07974; which are herein incorporated in their entirety by reference thereto.

TABLE 1

IN VITRO INHIBITORY ACTIVITY AND MINIMUM INHIBITORY CONCENTRATIONS (MIC) OF NATURAL AND SEMISYNTHETIC PRODUCTS AGAINST *M. TUBERCULOSIS* (H37RV).

| Compound | MIC (μg/mL) | % Inhibition |
|---|---|---|
| Manzamine A | 1.56 | 99 |
| ent-8-Hydroxymanzamine A | 3.13 | 99 |
| Manzamine E | 3.13 | 99 |
| (+)-8-Hydroxymanzamine A | <6.25 | 100 |
| ent-8-Hydroxymanzamine A diAc | <6.25 | 95 |
| 15, 16, 32, 33-tetrahydro-ent-8-hydroxymanzamine A | <6.25 | 100 |
| 8OHMA α-OH, Δ $^{15, 16}$ | <6.25 | 100 |
| 8OHMA β-OH, Δ $^{15, 16}$ | >6.25 | 61 |
| 8OHMA-Ac1 | <6.25 | 98 |
| 8OHMA-Ac2 | <6.25 | 95 |
| MA-Ac | >6.25 | 58 |
| Ircinal A | <12.5 | 98 |
| 8-HOMA Metabolite 1 | <12.5 | 98 |
| Manzamine J | <12.5 | 99 |
| 6-Deoxymanzamine X | <12.5 | 98 |
| Manzamine L | <12.5 | 99 |
| neo-Kauluamine | >12.5 | 44 |
| ent-Manzamine F | >12.5 |  |
| Rifampin | 0.25 | 100 |

TABLE 2

IN VITRO INHIBITORY ACTIVITY AND SELECTIVITY INDEX (SI) OF NATURAL AND SEMISYNTHETIC products against *P. falciparum*.
Cytotoxicity is measured against Vero cells.

| Compound | D6 Clone IC50 (ng/mL) |  | W2 Clone IC50 (ng/mL) |  | Cytotoxicity TC50 (ng/mL) |
|---|---|---|---|---|---|
| Chloroquine | 15.5 |  | 170.0 |  | >5,000 |
| Artemisinin | 10.0 |  | 6.3 |  | >5,000 |
| Manzamine A | 4.5 | SI = 64 | 8.0 | SI = 36 | 290 |
| (+) 8-Hydroxymanzamine A | 6.0 | SI = 53 | 8.0 | SI = 40 | 320 |
| Betacarboline 1 | 420 | SI > 11 | 720 | SI > 6.6 | >5,000 |

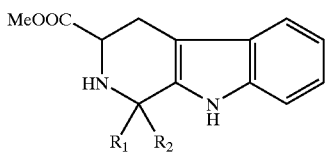

| | $R_1$ | $R_1$ | |
|---|---|---|---|
| | Me | Me | Betacarboline 1 |

TABLE 3

ANTI-HIV ACTIVITY OF THE MANZAMINE ALKALOIDS ASSAYED.

| Compound | HIV-1 in human PBM cells $EC_{50}$; μM | Cytotoxicity in human PBM cells $IC_{50}$, μM |
|---|---|---|
| Manzamine A | 12.9 | 5.1 |
| Manzamine E | 18.7 | 35.5 |
| (−)-12, 34-Oxamanzamine F | 20.4 | 75.2 |
| (−)-8-Hydroxymanzamine A | 44.2 | 4.9 |
| Ircinal A | 45.2 | 34.2 |
| (−)-Manzamine F | 94.8 | 40.8 |

Manzamine semisynthetic analogs. In an attempt to generate new semisynthetic manzamine analogs several routine chemical reactions were utilized starting with Manzamine A, Manzamine F and ent-8-hydroxymanzamine A. Of these, reaction of acetic anhydride in presence of excess sodium acetate at 80° C., for 30 minutes, under nitrogen, afforded the minor two new $\Delta^{34,35}$ products (9.8% and 1.5%) along with 8,12-di-O-acetyl ent-8-hydroxymanzamine A, as a major product (24%).

Reduction of ent-8-Hydroxymanzamine A using hydrazine hydrate in presence of Pd/carbon, in absolute ethanol for 12 hours, at room temperature, afforded a single major product (19%). The HRFTMS spectrum displayed molecular ion peak $(M+H)^+$ at m/z 569.3744, suggesting the molecular formula $C_{36}H_{49}N_4O_2$ 569.3856 and 15 degrees of double bond equivalence. The $^1H$- and $^{13}C$-NMR indicated the product is 15,16,32,33-tetrahydro-ent-8-hydroxymanzamine A as the olefinic proton and carbon signals 15, 16, 32, and 33 are replaced by upfield aliphatic signals.

Reduction of Manzamine F by sodium borohydride in anhydrous tetrahydrofuran at room temperature afforded two products (27.5%) and (6%). The HRFTMS spectra displayed molecular ion peaks $(M+H)^+$ at m/z 583.3100 and 583.3615, respectively suggesting the molecular formula $C_{36}H_{47}N_4O_3$ and 16 degrees of double bond equivalence. The broad proton singlets resonating at 3.77 and 3.86, respectively, were assigned the new oxygenated H-31. The β-orientation of H-31 is assigned based on comparison of its NOESY correlation with the β-oriented H-34. These compounds must then be the C-31 epimers, since the only spectral difference between both compounds is localized at C-31.

Manzamine antiinfective activities. Malaria. A single intraperitoneal (i.p.) dose of 100 μmoles/kg of ent-8-hydroxymanzamine A efficiently reduced parasitemia and increased the average survival days of P. berghei-infected mice to 9–11 days as compared with 2–3 days in the untreated controls and those treated with artemisinin. Mice treated with chloroquine survived for only 6 days with a comparable reduction of parasitemia at 100 μmoles/kg when compared with manzamine A and neo-kauluamine 2 days after treatment. The comparable reduction of parasitemia between manzamine A and chloroquine followed by a significant improvement in life expectancy in manzamine treated mice suggest that the immune stimulatory activity is key for the improvement seen in vivo. Three 50 μmoles/kg, i.p., doses of manzamine A was found to be curative and totally clears the parasite. Two oral doses (100 μmoles/kg) were shown to provide a 90% reduction of parasitemia when compared with control mice. Manzamine A, ent (−)-8-hydroxymanzamine A and neo-kauluamine all exhibit in vivo activity against P. berghei greater than chloroquine or artemisinin. See, Ang, K. K. H.; Holmes, M. J.; Higa, T.; Hamann, M. T.; Kara, U. A. K., "In Vivo and In Vitro Anti-Malarial Activity of the Beta-Carboline Alkaloid Manzamine A," Antimicrobial Agents & Chemotherapy 2000, 44, 1645–1649. In several cases mice treated with just a single dose of manzamine A (100 ||moles/kg) could completely clear the parasite. At this same dosage artemisinin and chloroquine treated animals had a life expectancy of 2–6 days. In addition the manzamine alkaloids were less toxic in vivo than chloroquine and also exhibit a significant immunestimulatory response with Plasmodium infected mice as seen by a dramatic increase in white blood cell populations. This immune response of infected mice treated with manzamine clearly warrants further scale-up isolations and detailed investigations into its mechanism of action.

To confirm the activity of the manzamines against malaria the World Health Organization examined manzamine A against the Plasmodium yoelii NS malaria strain in mice (Peters 4-day assay-Handbook of Animal Models of Infection Chapter 92, Academic Press 1999). In this model, Manzamine A had an ED50<5 mg/kg, and was more active than Na artesunate when given orally in either DMSO or a pharmaceutically more acceptable carboxy-methylcellulose-based formulation. Preliminary results also show that 8-hydroxymanzamine was active orally in DMSO (ED50<10 mg/kg against P. berghei N strain).

ent-8-Hydroxymanzamine A shows potent cytotoxicity against P-388 mouse lymphoma cells (IC50 0.25 μg/mL), while (+)-8-hydroxymanzamine A was reported inactive against the same cell line. This is a noteworthy indication of the improved bioactivity for the (−)-enantiomer. neo-Kauluamine possesses cytotoxicity with an IC50 1.0 μg/mL, against human lung and colon carcinoma cells, unlike the manzamine dimer kauluamine, which was inactive. This suggested that further oxygenation might improve the bioactivity and prompted additional lead-optimization through metabolism studies. Microbial metabolites (ircinal A and 8-HOMA metabolite 1) were less cytotoxic than the parent compounds and indicates the utility of biotransformation reactions to create new and potentially less toxic manzamine derivatives for leads against infectious pathogens.

Mtb. Most manzamines induced 98–99% inhibition of M. tuberculosis with MIC <12.5 μg/mL except manzamine F neo-kauluamine and several derivatives, which indicated that additional oxygenation of the azacyclooctane ring reduces the TB activity. The activity of ircinal A indicates that the β-carboline moiety is not essential for activity in vitro however ircinal A failed to show any activity in vivo against malaria. These results suggest the candidacy of ircinal A as a possible antimalarial/antituberculosis lead for further development by utilizing the Pictet-Spengler reaction to generate a series of beta carboline and isoquinoline analogs. The in vitro activity of natural, semisynthetic and biocatalytically-derived manzamines against M. tuberculosis (H37Rv) is reported in Table 1. neo-Kauluamine, the second manzamine dimer with two β-oriented ether bonds bridging both monomers at C-31/C-34' and C-30'/C-34 carbons of azacyclooctane site, in addition to two free α- and β-hydroxyl groups at C-30 and C-31', respectively also displayed less activity (44% inhibition). This suggests that α-hydroxylation at C-31 greatly enhances the activity while β-hydroxylation at this position reduces the activity. Reduction of both $\Delta^{15,16}$ and $\Delta^{32,33}$ systems has no effect on the activity and substitution at C-33 improves activity against Mtb. The dimer neo-kauluamine shows activity against malaria in mice which is comparable with manzamine A and ent-8-hydroxy manzamine A.

The aliphatic portion of this alkaloid appears to be the key pharmacophore for antiMtb and antimalarial activity in vitro with the beta carboline also contributing to the activity in vivo (malaria). As a result the aldehyde of ircinal A may be utilized as a starting material to generate a tremendous number of bioactive derivatives originating from this functionality. These derivatives may be utilized for the treatment of infectious disease as well as cancer and inflammatory diseases as outlined in earlier patents. The oxidation, reduction, formation of Schiff's bases, etc. at the aldehyde position is virtually endless. The primary focus however will be to utilize the aldehyde for the formation of additional heterocyclic moieties. See, Joule, J. A.; Mills, K.; Smith, G. F. "*Heterocyclic Chemistry*" Third Edition 1995 pp Chapman & Hall, New York. If, for some reason, a retro Pictet-Spengler condensation can not be made to work there will be sufficient quantities of ircinal A available by isolation from the sponges to study the chemistry at this position. A valuable aspect of this project is that through the molecular and microbiology proposed earlier a genetically engineered route to ircinal A is also conceivable. The goal of the semisynthesis will be to focus on the introduction of additional heteroaromatic functionality at the aldehyde position. A valuable result of this project will be additional synthetic methodologies using the Pictet-Spengler reaction for the formation of complex alkaloids semisynthetically.

BRIEF DESCRIPTION OF THE FIGURES

*Toxoplasma gondii*. Mice infected with a lethal dose of *T. gondii* (10 cysts of the C56 strain given orally) and treated intraperitoneally with manzamine A (8 mg/kg once a day for 8 days starting one day after infection) had a significant prolongation of time to death. Additionally, when all control mice had died by day 16 of infection, all the manzamine A treated mice were alive. Untreated infected mice in the control group started dying 10 days post infection. Mice treated with manzamine A died nine days after treatment stopped. This data clearly indicate that manzamine A was capable of controlling the infection for the duration of the treatment and an optimized treatment regime may yield improved results. It is important to note that no uncommon signs or behavior of the mice occurred during the treatment (paralysis, blindness, twirling). FIGS. 1 and 2 provide the graphic results of this experiment. FIG. 1 shows EXP 398B(99)-effect of intraperitoneal manzamine A on surival of SW mice infected orally with 10 C56 Cysts of *T. Gondii*. Treatment was begun on Day 1 following in infection and continued for 8 days. FIG. 2 shows the cumulative survival of the control group and treated group.

Materials and Methods

Figure 1:
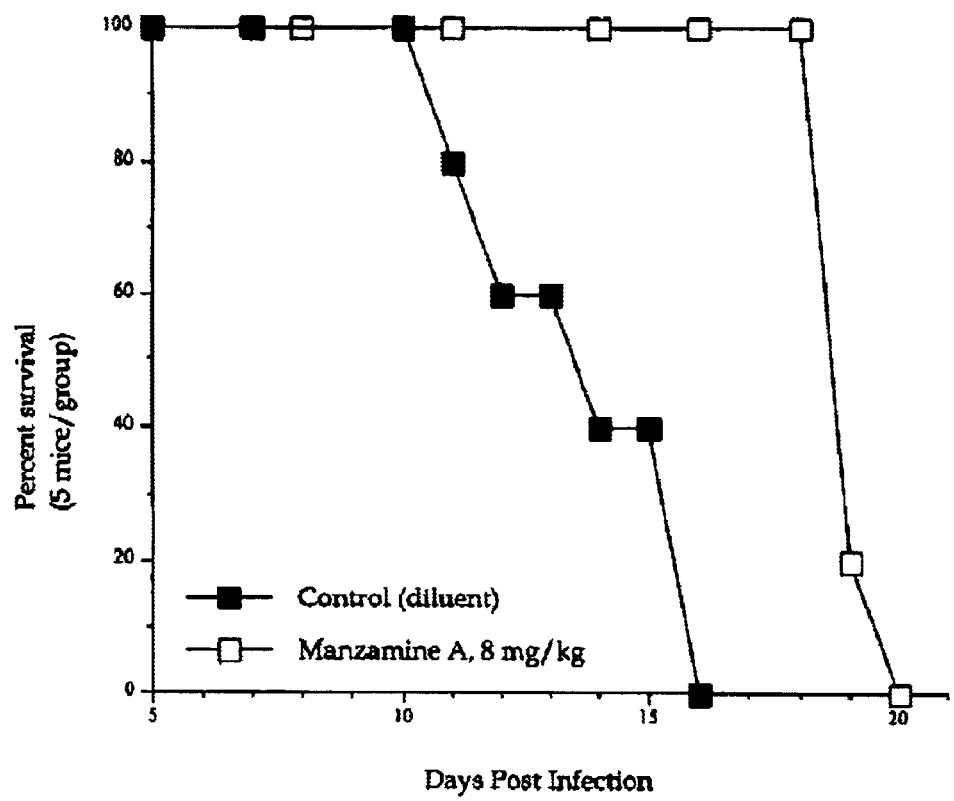
FIG. 1 shows EXP 398B(99)-Effect of intraperitoneal manzamine a on surival of SW mice infected orally with 10 C56 of *T. Gondii*, Treatment was begun on Day 1 following in infection and continued for 8 days.
Figure 2:
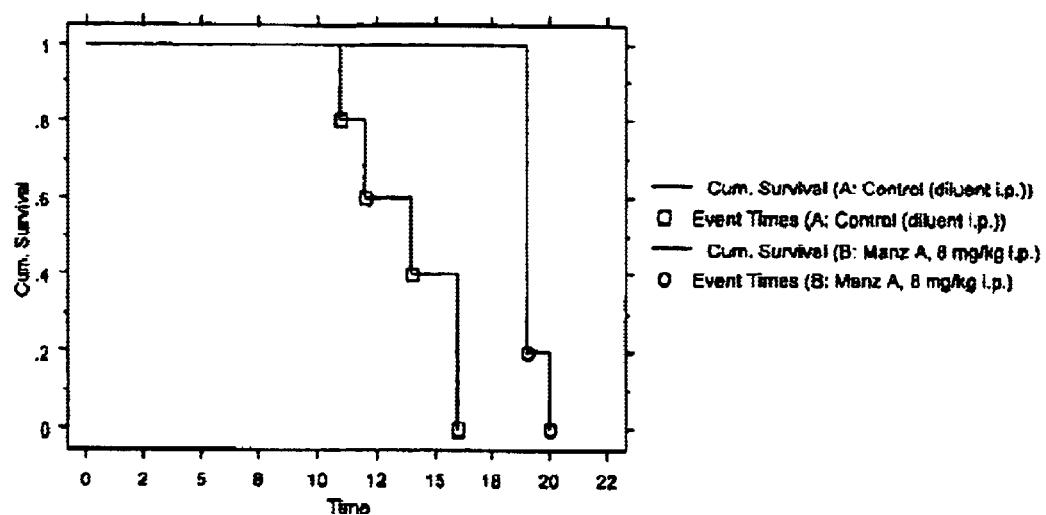
FIG. 2 shows the cumulative surival of the control group and treated group.

In Vitro Evaluation of Antimalarial Activity. (University of Mississippi's National Center for Natural Products Research.) Stock cultures of the Sierra Leone D6 clone (chloroquine-sensitive, mefloquine-resistant) and Indochina W2 clone (chloroquine-resistant, mefloquine sensitive) of *P. falciparum* are maintained using a modification of the method of Trager and Jensen (1976). The organisms are grown continuously in A+ human red blood cells (obtained monthly fresh from Mississippi Blood Services) in RPMI 1640 medium containing 25 mM HEPES buffer, L-glutamine, 27 mM bicarbonate, 60 µg/mL amikacin and 10% normal A+ human plasma (clarified by centrifugation and heat-inactivated at 56° C. for 30 min). The cultures are maintained in a 25 cm$^2$ tissue culture flask (Corning Glass Works, Corning, N.Y.) containing 5 mL of RPMI 1640 complete growth medium with a 6% erythrocyte suspension. The flasks are flushed aseptically with a gas mixture consisting of 90% $N_2$, 5% $O_2$, 5% $CO_2$ (Standard Welders, Jackson, Miss.), sealed and incubated at 37° C. for approximately 24 h. The organisms are subcultured daily, which involves careful removal of the old growth medium, making a smear of the infected red blood cells, and staining the smear with Giemsa stain to determine the percent (%) parasitemia of the culture. The smears are analyzed using the 100× oil immersion objective of an Olympus BHT Brightfield Microscope ($C^2$ Corporation, Hialeah, Fla.). Once the parasitemia is determined, a portion of the infected erythrocytes is discarded and fresh uninfected erythrocytes and growth medium are added to each flask and treated as previously described.

The extracts and compounds are dissolved to a final concentration of 50 and 5 mg/mL respectively, in DMSO or EtOH. Serial three-fold dilutions are made of each sample in complete growth medium using a Matrix Electrapette Liquid Handling System (Matrix Technologies, Lowell, Mass.) and then added in duplicate to the 96-well microtiter plates containing each clone of *P. falciparum*. The final concentrations in the wells are 119,000 ng/mL, 39,666 ng/mL and 13,222 ng/mL for extracts and 11,900 ng/mL, 3,966 ng/mL and 1,322 ng/mL for pure compounds. The concentration of DMSO and EtOH is fixed in each well at 0.2%, which has no effect on the growth of the parasite. Chloroquine diphosphate (Sigma Chemical Co., St. Louis, Mo.), Mefloquine HCl (Roche Laboratories, NY) and Arteether (Pharmacognosy Dept., Univ. of MS, USA) are used as control drugs.

Microtiter plate preparations. Each clone is adjusted with fresh A+ uninfected red blood cells and complete growth medium to yield a 2% hematocrit and a 2% parasitemia. See, Desjardins, R. E., Canfield, C. J., Haynes, J. D., Chulay, J. D, *Antimicrob. Agents Chemother.* 1979, 16, 710. Two microtiter plates are prepared for each 12 tested samples. One plate contains the D6 clone and other the W2 clone. The suspensions of each clone are added in 200 µL aliquots to all wells of the 96-well plates except for the following wells: G1–2, H1–2: medium blanks; G3–4, H3–4: uninfected RBC control. Ten µL aliquots of each drug dilution are added to adjacent wells on each microtiter plate using a Matrix Electrapette Liquid Handling system (Matrix Technologies, Lowell, Mass.). The plates are then placed in an airtight, humidified Modular incubator (Billups-Rothenberg Del Mar, Calif.), flushed with the gas mixture of 90% $N_2$, 5% $O_2$, 5% $CO_2$ and incubated at 37° C. for approximately 48 h.

Parasite LDH assay. After a 48-hour incubation, the cultures are resuspended and 20 µL aliquots are removed from each well and transferred to the corresponding wells of another 96-well microtiter plate that contains 100 $\mu$L aliquots of Malstat reagent (Flow, Inc., Portland, Oreg.). The plates are incubated for approximately 20 min and then 20 $\mu$L of a 20:1 mixture of nitroblue tetrazolium and phenazine ethosulfate (1 mg and 0.05 mg/mL, respectively) (Sigma Chemical Co., St. Louis, Mo.) is added to each well of the microtiter plates. The plates are incubated for approximately 60 minutes or longer until the tetrazolium salt is sufficiently reduced to a blue formazan product. The reaction is stopped by addition of 100 $\mu$L of 5% acetic acid to each well of the microtiter plates. The plates are analyzed by reading the endpoint at 630 nm on a Biotek 312e Microplate Reader (Fisher Scientific, Norcross, Ga.). See, Makler, M. T.; Ries, J. M.; Williams, J. A.; Bancroft, J. E.; Piper, R. C.; Gibbins, B. L.; Hinrichs, D. J., *Am. J. Trop. Med. Hyg.* 1993, 48, 739.

False negative results which might be induced by the chemical reduction of the dye by the marine extract components is avoided by preliminary testing of these tested extracts without malaria which revealed no such chemical reaction with the Malstat reagent or the NBT/PES. The false positive result that might originate from parasite LDH inactivation by the extract contents is avoided by cloning the parasite LDH as a standard. Positive extracts are then tested to see if there is a general inactivation of the enzyme. In addition, erythrocytes are removed from those wells that are positive for antimalarial activity and from smears made to determine if the parasite had been killed.

In vitro Cytotoxicity to Mammalian Cells. Vero cells (ATCC #CCL 81) are obtained from the American Type Culture Collection. The Vero cells served as an indicator of general cytotoxicity. Vero cells are grown in RPMI 1640 medium (Sigma Chemical Co., St. Louis, Mo.) supplemented with glutamine, sodium bicarbonate and 10% fetal calf serum (Hyclone Laboratories) at 37° C. in a 5% $CO_2$ humidified atmosphere. The cells are allowed to grow for 48–72 h, at which time the cells are subcultured. The cells are dissociated by trypsinization with 0.25% trypsin and resuspended in a volume of growth medium to achieve a concentration of approximately 500,000 cells/mL. Approximately 100 $\mu$L of the cells are added to each well of a 96 well microtiter plate to achieve a final concentration of 50,000 cells per well. The plate containing the cells is incubated for approximately 24 h and then, serial dilutions of the tested extracts (same concentrations as antimalarial assay) are made and added to duplicate wells. The cells are incubated with the test samples for an additional 48 h and the viability of the cells is determined relative to control wells. Amphotericin B is used as a positive control. The neutral red assay is used to determine the viability of the cells. See, Borenfreund, E.; Babich, H.; Martin-Alguacil, N., *In vitro Dev. Cell. Biol.* 1986, 26, 449. The plates are read on a Bio-Tek Model 312e microplate reader.

In Vivo Evaluation of Antimalarial Activity. (National University of Singapore by Dr. Kenny Ang, confirmation of activity at the WHO). Four-week-old, male Swiss albino mice are injected intraperitoneally with $10^7$ *P. berghei*-infected mouse erythrocytes. On day 2 after infection, mice are treated with a single intraperitoneal injection of either the test compound or a reference drug (chloroquine or artemisinin) within a concentration range of 50 to 1,000 $\mu$mol/kg of body weight. All test compounds and reference drugs were injected as a suspension in 5% Tween 60 saline. For oral administration, the test compounds are given as a suspension in corn oil, and mice are given two consecutive doses of test compound at 100 $\mu$mol/kg on days 2 and 3 after infection. Control mice received the drug on days 2 and 3 after infection. Control mice receive only 5% Tween 60 saline or corn oil. Survival of mice was recorded daily. Percent parasitemia is determined microscopically (magnification, ×1,000) from mouse-tail blood smears that were fixed with methanol and stained with Giemsa stain. Blood samples from individual *P. berghei*-infected mice were collected at various times after a single intraperitoneal treatment of 100 $\mu$mol/kg of manzamine A per kg on day 3 after infection. For transmission electron microscopy, approximately 0.5-ml blood samples are fixed with 3% glutaraldehyde in 0.1 M cacodylate buffer (pH 7.4), post-fixed with 1% osmium tetroxide and 1% uranyl acetate, dehydrated in a graded ethanol series, and embedded in Spurr's resin. The resulting blocks are cut by using a Reichert-Jung Ultracut with a glass knife. Ultra thin sections were mounted on 150-mesh copper grids, stained with 1% uranyl acetate and 1% lead citrate, and examined with a JEM-100CX electron microscope. Manzamine in plasma was detected by liquid chromatography=selected reaction monitoring-mass spectrometry (LC-SRM-MS). *P. berghei*-infected mice will be treated with the alkaloid (100 $\mu$mol/kg intraperitoneally) on day 3 post infection. Blood samples are collected from individual mice at specific times up to 48 h posttreatment. Plasma was isolated by centrifugation and extracted with 95% acetonitrile containing 5 mM ammonium acetate. The plasma extract was filtered, and 5 $\mu$l samples are injected into a Shimadzu LC-10 AD microbore high-pressure liquid chromatograph interfaced with a Perkin-Elmer API 300 turbo-ion-spray tandem mass spectrometer. Samples are separated on a Prodigy C-18 column (30 by 1 mm, 5-$\mu$m inner diameter) by elution at 50 $\mu$l/min with 86% acetonitrile containing 5 mM ammonium acetate. Manzamine can be detected by monitoring the transition of the protonated manzamine precursor ion from the $(M+H)^+$ to the $(M+H —H_2O)^+$. Peak areas for the product ion chromatograms are integrated, and concentrations are determined from a linear calibration curve for manzamine in spiked plasma. The limit of detection for the manzamines in plasma by LC-SRM-MS is 2.5 pg. Results are subjected to a nonparametric statistical assessment with a confidence interval of 99% (p<0.01) by using Analyse-it software linked to Microsoft Excel. The program uses the Mann-Whitney U test to determine significant differences between two groups of data.

In Vitro Evaluation of Antimycobacterial Activity. (Tuberculosis Antimicrobial Acquisition & Coordinating Facility (TAACF)). Primary evaluation of purified compounds will be conducted at 6.25 $\mu$g/mL (or molar equivalent of highest molecular weight compound in a series of congeners) against *Mycobacterium tuberculosis*$H_{37}$Rv (ATCC 27294) in BACTEC 12B medium using a broth microdilution assay, the Microplate Alamar Blue Assay (MABA). Compounds exhibiting fluorescence are tested in a BACTEC 460 radiometric system. See, Collins, L.; Franzblau, S. G. "Microplate Alamar Blue Assay versus BACTEC 460 System for High-throughput Screening of Compounds against *Mycobacterium tuberculosis* and *Mycobacterium avium*", *Antimicrob. Agents Chemother.* 1997, 41, 1004–9. Marine compounds (>0.7 mgs) showing <90% inhibition in the primary screen (MIC>6.25 $\mu$g/mL) will not be evaluated further. Marine natural products or semisynthetics demonstrating at least 90% inhibition in the primary screen will be reassayed at lower concentrations against *M. tuberculosis* $H_{37}$Rv to determine an actual MIC using MABA. The MIC is defined as the lowest concentration effecting a reduction in fluorescence of 90% relative to controls. Along with the determination of MICs, the compounds will be tested for cytotoxicity ($IC_{50}$) in VERO cells at concentration ≦62.5 μg/mL or $10^X$ the MIC for *M. tuberculosis* $H_{37}Rv$ (solubility in media permitting). After 72 hours of exposure, viability is measured on the basis of cellular conversion of MTT into a formazan product using the Promega CellTiter 96 Non-radioactive Cell Proliferation Assay. Compounds for which the selectivity index (i.e., $IC_{50}$:MIC ratio) SI>10 will have in vitro activity confirmed in the BACTEC 460 at 6.25 μg/mL. Compounds are then tested for killing of *M. tuberculosis* Erdman (ATCC 35801) in monolayers of mouse bone marrow macrophages See, Skinner, P. S.; Furney, S. K.; Jacobs, M. R.; Klopman, G.; Ellner, J. J.; Orme, I. M., "A Bone Marrow-Derived Murine Macrophage Model for Evaluating Efficacy of Antimycobacterial Drugs under Relevant Physiological Conditions," *Antimicrob. Agents Chemother.* 1994, 38, 2557–63. ($EC_{90}$ and $EC_{99}$; lowest concentration effecting a 90% and 99% reduction, respectively, in colony forming units at seven days compared to drug-free controls) at 4-fold concentrations equivalent to 0.25, 1, 4 and 16× the MIC. At the same time that compounds are being assayed in macrophages, MICs are determined in the MABA against a strain of *M. avium* (ATCC 25291) and against three strains of single-drug-resistant (SDR) *M. tuberculosis*. The natural products and derivatives may be tested against TB strains resistant to isoniazid (ATTC 35822), rifampin (ATCC 35838), and one additional SDR strain chosen on the basis of the structural class of the marine natural product; confirmatory testing also occurs against drug-sensitive *M. tuberculosis* $H_{37}Rv$ and Erdman. The minimum bactericidal concentration (MBC) will be determined for *M. tuberculosis* $H_{37}Rv$ and Erdman by subculturing onto drug-free solid media and enumerating colony forming units following exposure in supplemented Middlebrook 7H9 media to drug concentrations equivalent to and higher than the previously determined MICs of the respective strains. The initial MIC determination can be accomplished with as little as 0.7 mgs, with the remainder of the in vitro evaluations requiring about 10mgs.

In Vivo Evaluation of Anti-*M. avium* Activity. (TAACF assay) The evaluation of marine derived compounds against *M. avium* is available for compounds showing an *M. avium* MIC ≦6.25 μg/mL. An expanded primary screen is conducted at a range of 1 μg/mL–64 μg/mL against five *M. avium* clinical isolates (100, 101, 108, 109, 116) in Middlebrook 7H9 broth using the MABA and BACTEC 460 systems. Those compounds with an MIC ≧8 μg/mL in at least three of the five strains tested are reassayed at lower concentrations against 30 strains, including five strains resistant to clarithromycin. Those marine derived compounds demonstrating significant activity against the panel are tested for intracellular activity in an infected macrophage model using the human monocyte cell line U937, against three *M. avium* strains (100, 101, 109) representing the three serotypes encountered in AIDS patients. If activity is seen against any of the strains, ethambutol (4 μg/mL) is added in combination with the lowest concentration of the evaluated compound that showed activity in order to examine potential synergism. For promising molecules, in vivo activity is studied in a mouse model for *M. avium* infection. Beige-C57BL/j bg female mice are infected i.v. with $3510^7$ cfu of *bacilli*. After one week, therapy is initiated and continued for four weeks. The liver and spleen are then aseptically dissected, weighed, and homogenized. Serial dilutions are plated onto 7H11 agar for quantitative culture. For the in vitro evaluation of marine derived compounds against *M. avium* 25–30 mgs will be required.

What is claimed is:

1. A method of treating an infectious disease or condition caused by bacteria in a subject in need of such treatment comprising administering to the subject an effective amount of a manzamine, manzamine derivative or analog or an optical isomer or racemate or tautomer thereof or a pharmaceutically acceptable salt thereof.

2. The method according to claim 1, wherein the bacteria is *Enterococcus coil, E. faecalis, Bacillus subtilus, Staphylococcus aureus, S. epidermidis, Pseudomonas aeruginosa, Trichophyton mentagrophytes, Streptococcus pyogenes, Salmonella sp., Mycobacterium tuberculosis* or *M. intracellulare.*

3. The method according to any one of claim 1 or 3 or wherein the manzamine or manzamine derivative or analog is Manzamine A, ent-8-Hydroxymanzamine A, Manzamine E, (+)-8-Hydroxymanzamine A, ent-8-Hydroxymanzamine A diAc 15,16,32,33-tetrahydro-ent-8-hydroxymanzamine A, 8OHMA α-OH, $\Delta^{15,16}$, 8OHMA β-OH, $\Delta^{15,16}$, 8OHMA-Acl, 8OHMA-Ac2, MA-Ac, Ireinal A, 8HOMA Metabolite 1, Manzamine J, 6-Deoxymanzamine X, Manzamine L, neo-Kauluamine, ent-Manzamine F.

* * * * *